United States Patent
Kim

(10) Patent No.: US 9,126,008 B2
(45) Date of Patent: Sep. 8, 2015

(54) CATHETER AND METHOD FOR ITS USE

(71) Applicant: Sungyul D Kim, Lexington, MA (US)

(72) Inventor: Sungyul D Kim, Lexington, MA (US)

(*) Notice: Subject to any disclaimer, the term of this patent is extended or adjusted under 35 U.S.C. 154(b) by 197 days.

(21) Appl. No.: 13/913,647

(22) Filed: Jun. 10, 2013

(65) Prior Publication Data

US 2013/0331824 A1 Dec. 12, 2013

Related U.S. Application Data

(60) Provisional application No. 61/657,853, filed on Jun. 10, 2012.

(51) Int. Cl.
*A61M 25/00* (2006.01)
*A61M 25/10* (2013.01)

(52) U.S. Cl.
CPC ....... *A61M 25/0017* (2013.01); *A61M 25/0026* (2013.01); *A61M 25/10* (2013.01); *A61M 25/1002* (2013.01); *A61M 25/1011* (2013.01); *A61M 25/0097* (2013.01); *A61M 2025/1004* (2013.01)

(58) Field of Classification Search
CPC ............ A61M 25/0017; A61M 25/1011; A61M 25/0026; A61M 25/0097; A61M 2025/1015; A61M 2025/1047; A61M 2025/1065; A61M 2025/1072; A61M 2025/1093; A61M 2210/1078; A61M 2210/1085; A61M 2210/1089; A61M 25/007; A61M 25/0071; A61M 25/1002; A61M 25/10; A61M 2025/1004
See application file for complete search history.

(56) References Cited

U.S. PATENT DOCUMENTS

| | | | |
|---|---|---|---|
| 3,421,509 A | 1/1969 | Fiore | |
| 3,438,375 A | 4/1969 | Ericson | |
| 3,811,448 A | 5/1974 | Morton | |
| 4,022,216 A | 5/1977 | Stevens | |
| 4,154,242 A | 5/1979 | Termanini | |
| 4,217,903 A | 8/1980 | Witherow | |
| 4,233,983 A * | 11/1980 | Rocco | 604/97.01 |
| 4,575,371 A | 3/1986 | Nordqvist et al. | |
| 4,701,162 A | 10/1987 | Rosenberg | |
| 4,781,677 A * | 11/1988 | Wilcox | 604/28 |
| 4,820,270 A | 4/1989 | Hardcastle et al. | |

(Continued)

FOREIGN PATENT DOCUMENTS

| | | | | |
|---|---|---|---|---|
| GB | 2245499 A | * | 1/1992 | ............ A61M 25/10 |
| WO | WO 2007/005734 | | 1/2007 | |

OTHER PUBLICATIONS

Milles, George, "Catheter-Induced Hemorrhagic Pseudopolyps of the Urinary Bladder," Journal of the American Medical Association, 193(11)JAMA 968-69 (1965).

(Continued)

*Primary Examiner* — Adam Marcetich
(74) *Attorney, Agent, or Firm* — Cesari and McKenna, LLP; William J. Mostyn

(57) ABSTRACT

The present invention discloses a catheter and method of using a catheter with two balloons and at least one inlet opening located on the proximal end of the catheter. The two balloons are adapted to retain the catheter within the body cavity and facilitate the flow of gases and fluids into one or more inlet openings. The invention also provides inlet openings located at different levels of the catheter tube to allow for complete drainage of fluid from the body cavity. The unique design of the present invention provides complete drainage of a body cavity and reduces damage and trauma to the body cavity.

21 Claims, 7 Drawing Sheets

(56) References Cited

U.S. PATENT DOCUMENTS

| | | | |
|---|---|---|---|
| 4,973,301 | A | 11/1990 | Nissenkorn |
| 5,096,454 | A | 3/1992 | Samples |
| 5,295,960 | A * | 3/1994 | Aliahmad et al. ........ 604/103.11 |
| 5,308,323 | A * | 5/1994 | Sogawa et al. ............. 604/95.03 |
| 5,350,361 | A * | 9/1994 | Tsukashima et al. .... 604/103.07 |
| 5,417,657 | A * | 5/1995 | Hauer ...................... 604/103.02 |
| 5,441,485 | A * | 8/1995 | Peters ...................... 604/101.01 |
| 5,769,818 | A | 6/1998 | El Maoued |
| 6,096,013 | A | 8/2000 | Hakky et al. |
| 6,527,737 | B2 | 3/2003 | Kaneshige |
| 6,837,868 | B1 | 1/2005 | Fajnsztajn |
| 7,264,609 | B2 | 9/2007 | Hakky et al. |
| 2002/0107540 | A1 * | 8/2002 | Whalen et al. ................. 606/192 |
| 2005/0186370 | A1 * | 8/2005 | Hamilton et al. ............. 428/35.2 |
| 2005/0228402 | A1 * | 10/2005 | Hofmann ...................... 606/108 |
| 2006/0167438 | A1 * | 7/2006 | Kalser et al. .................. 604/544 |
| 2008/0103443 | A1 * | 5/2008 | Kabrick et al. .......... 604/103.07 |
| 2008/0125757 | A1 | 5/2008 | Gobel |
| 2009/0030370 | A1 * | 1/2009 | Nishtala et al. .......... 604/103.01 |
| 2009/0171317 | A1 * | 7/2009 | Versi ............................. 604/517 |
| 2009/0221992 | A1 | 9/2009 | Hannon et al. |
| 2011/0082444 | A1 * | 4/2011 | Mayback et al. ............. 604/544 |
| 2011/0098683 | A1 | 4/2011 | Wiita et al. |

OTHER PUBLICATIONS

Zink, Peter et al., "Twin Balloon Catheter: Solution to the Foley Catheter Design Faults," The Wallace H. Coulter Translational Partners Grant Program, Apr. 14, 2013, 13 pages.

Ekelund, P. et al, "The Reversibility of Catheter-Associated Polypoid Cystitis," Journal of Urology, vol. 130, Sep. 1983, pp. 456-459.

Leuck, A. et al, Complications of Foley Catheters—Is Infection the Greatest Risk,: Jurology, vol. 187, 1662-1666, May 2012.

Parkin, et al, "Indwelling catheter-associated urinary tract infections," British Journal of Community Nursing, 2003, vol. 8, No. 4. pp. 166-171.

Glahn, et al, "Influence of Drainage Conditions on Mucosal Bladder Damage by Indwelling Catheters," Scand J Urol Nephrol 22:93-99, 1988.

* cited by examiner

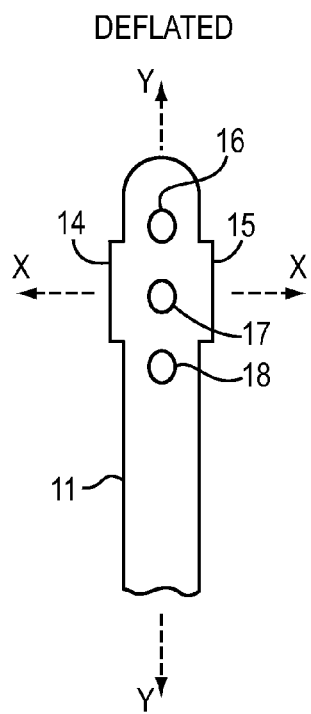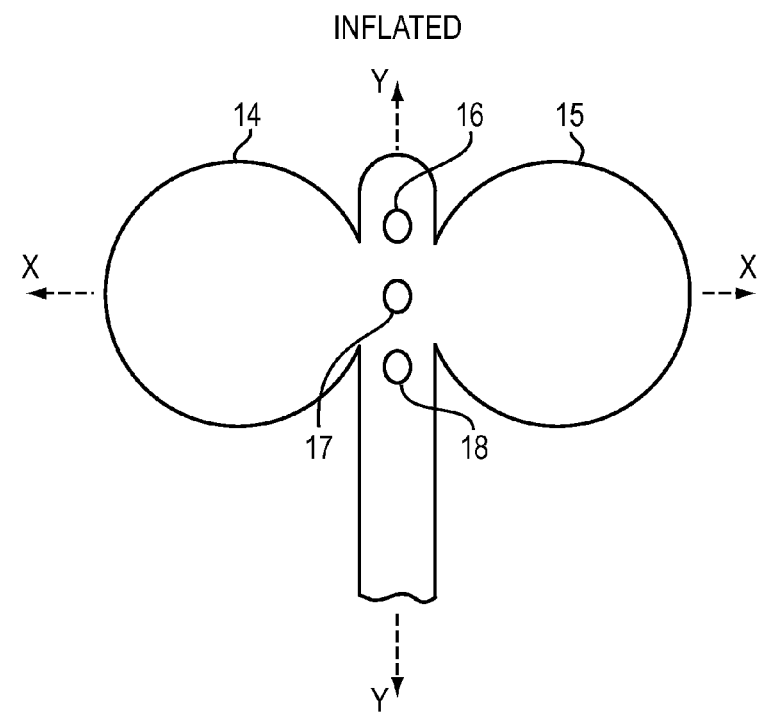
FIG. 3A  FIG. 3B
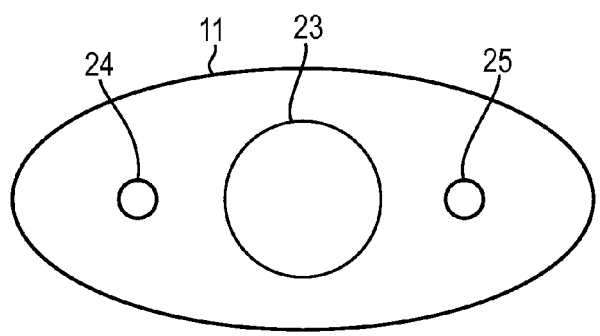
FIG. 4

CATHETER AND METHOD FOR ITS USE

CROSS-REFERENCE TO RELATED APPLICATIONS

The present application claims the benefit of U.S. Provisional Patent Application Ser. No. 61/657,853, which was filed on Jun. 10, 2012, by Dr. Sungyul D. Kim for a TWIN BALLOON CATHETER and is hereby incorporated by reference.

BACKGROUND OF THE INVENTION

1. Field of the Invention

The invention relates generally to catheters for insertion into body cavities. More particularly, the invention is directed to a catheter with at least one inlet and two balloons for self-sustaining the catheter within a body cavity.

2. Background Information

Catheters are generally used in medicine to drain fluid from various body cavities. For purposes of describing the present invention, a urinary catheter is discussed. However, the same features may be applied to different catheters used to drain fluids from other body cavities.

Indwelling urinary catheters are used to treat certain medical conditions in which a patient cannot properly urinate. Such conditions may include urinary incontinence, urinary retention, trauma or problems caused by other medical conditions. By helping to void the bladder, indwelling urinary catheters facilitate the removal of waste products, such as ammonia, bilirubin and creatinine, and foreign substances, such as microbes and fungi, from the body. Indwelling urinary catheters may also be used after a major trauma or surgical procedure to drain the bladder or divert urine away from the bladder. For example, urine and blood may be diverted away from the bladder following prostate or bladder surgery. Indwelling urinary catheters are also used to assess kidney function by monitoring urine output.

The most commonly used indwelling urinary catheter is the Foley catheter. It comprises a flexible tube which extends from outside the body into the urinary bladder through the urethra. The Foley catheter comprises a main lumen and much smaller secondary lumen. The main lumen acts as a conduit to facilitate the removal of urine from the bladder and the smaller lumen is used to deliver a sterile liquid into a singular annular balloon located within the bladder above the opening of the urethra. The balloon is located near the tip of the Foley catheter and serves to retain the catheter inside the bladder. The tip of the Foley catheter also contains a urine inlet opening located above the balloon.

Although the Foley catheter is the most commonly used catheter, it has many inherent drawbacks which render it unsafe and undesirable. One major shortcoming of the Foley catheter is its inability to fully drain the bladder of urine. The pointed catheter tip and the urine inlet of the Foley catheter remain above the balloon thus causing urine to collect around the periphery of the balloon. As the urine is drained through the large lumen of the catheter, a residual volume of urine is unable to escape the bladder through the urine inlet and thus remains in the bladder. This residual volume of urine may cause serious problems for patients including the accumulation and proliferation of pathogenic organisms within the bladder which may render the patient susceptible to subsequent infection or harm to bladder and kidney tissue.

The Foley catheter may also directly damage the tissue of the bladder. For example, movement by the patient or catheter itself may result in the Foley catheter tip contacting, rubbing, irritating, or otherwise damaging the mucosal lining of the bladder, including causing lesions, bleeding, scarring and the like. Further, as the urine exits the bladder through the main lumen of the Foley catheter, a negative pressure differential is created between the main lumen and the bladder. This negative pressure differential creates a suction effect which pulls the mucosa of the bladder into the Foley catheter's urine inlet opening thus damaging the mucosal lining of the bladder. Such damage may include hemorrhagic pseudopolyps within the urinary bladder as reported by Milles, G., *Catheter-Induced Hemorrhagic Pseudopolyps of the Urinary Bladder*, Journal of the American Medical Association, 193(11) JAMA 968-69 (1965). Additionally, any damage to the bladder's mucosal lining caused by the Foley catheter tip may subsequently lend itself to infection by offending organisms introduced into the bladder during normal urine production or by the microbes and other pathogens present in the residual urine that has accumulate due to incomplete draining by the Foley catheter. This damage provides easy access for microbes and fungi around the normal protective tissue layers of the bladder. Therefore, the Foley catheter is both unsafe and undesirable.

Other prior art catheters do not solve all of these problems. For example, the catheter described in Nordqvist et al. ("Nordqvist") (U.S. Pat. No. 4,575,371) does not allow for full drainage of the bladder. Nordqvist uses a single, expandable balloon that projects past the catheter tip, which is designed to prevent catheter-tip-induced injury to the mucosal wall. However, the Nordqvist single balloon may slip out of the bladder because the single balloon projects past the catheter tip resulting in an inverted mushroom-shaped configuration that is easier than, for example, the Foley catheter, to slip out of the bladder. Further, the Nordqvist catheter does not allow for complete draining of the bladder because, for example, there is no distal urine inlet at or below the distal side of the single balloon. In fact, Nordqvist places the urine inlet above the single balloon because Nordqvist states that locating the hole below the single balloon will not allow for continuous drainage due to the bladder wall closing around the single balloon. Further, the Nordqvist catheter would not allow for complete draining if, for example, the catheter shifted and urine flowed around the single balloon because the balloon completely surrounds the proximal end of the catheter thus acting as a stopper for any urine that may become trapped below the single balloon and there is no urine inlet below the balloon. The alternative embodiment described by Nordqvist wherein the single balloon contains two compartments does not cure this defect because it is still a single balloon that completely surrounds the proximal end of the catheter thus trapping urine below this single balloon and retaining a residual volume of urine in the bladder.

In Morton (U.S. Pat. No. 3,811,448), the urine inlet is located below a single balloon that is inflated on one side of the proximal end of the catheter. A urine inlet is located above and below this balloon on the side of the catheter tube that is opposite the balloon. However, as the bladder contracts upon voiding of the bladder, it conforms to the shape of the balloon. Thus, when the bladder contracts it disrupts the bowed shape of the Morton catheter by fully surrounding the single balloon and preventing urine from flowing into the distal inlet. This slows down the rate of voiding because there are less urine inlets. Further, as the bladder contracts, the catheter tube and tip contact the side of the bladder wall thus damaging the mucosal layer of the bladder. For example, the tube and tip of the Morton catheter may rub against the mucosal lining of the bladder and the mucosal lining may be pulled into both urine inlets due to the negative pressure differential between the bladder and the lumen of the catheter. Additionally, when the bladder contracts and surrounds the single balloon of the Morton catheter, a residual volume of urine remains above the balloon because the urine inlet located above the balloon is situated a certain distance away from the balloon. Therefore, a residual volume of urine will reside under the proximal urine inlet opening. Accordingly, the catheter described in Morton is unsafe and undesirable.

The Duette catheter (US 2011/0098683 A1) utilizes two balloons located on a catheter tube with one balloon above the other balloon and wherein each balloon fully surrounds the catheter tube. A urine inlet is located between the two balloons. However, the Duette catheter retains the same configuration as the Foley catheter within the bladder and the urine inlet is located above the retention balloon. Thus, the Duette catheter is equally ineffective at fully draining the bladder and a residual volume of urine remains in the bladder.

In addition to the above-mentioned drawbacks, the prior art devices have large surface areas. As such, these prior art devices are prone to the formation of biofilms on their surfaces. These biofilms act as breeding grounds for the proliferation microorganisms within the body cavity and thus expose the patient to an increased risk of infection.

BRIEF DESCRIPTION OF THE DRAWINGS

The invention description below refers to the accompanying drawings, of which:

FIGS. 3A and 3B are enlarged views of the proximal catheter tip of FIG. 2 with the balloons deflated and inflated;

FIG. 4 is a cross-sectional view of the catheter tube 11 of FIG. 2;

DETAILED DESCRIPTION OF AN ILLUSTRATIVE EMBODIMENT

The present invention provides a catheter without the above-mentioned drawbacks. The invention provides a catheter with two balloons located on the proximal end of the catheter and at least one inlet opening. The two balloons are inflated to retain the catheter within the body cavity and are configured to facilitate the flow of fluids or gases into one or more inlet openings. The invention provides an inlet or inlet openings located at different levels of the catheter tube to allow for complete drainage of fluid from the body cavity. The two balloons are configured to prevent the catheter tip from touching the bladder wall and maintain enough distance between the inlets and the bladder wall to thereby prevent mucosa from being drawn into any inlet.

For purposes of describing the illustrative embodiments of this invention, the terms as used herein, such as "proximal," "distal," "top," "bottom," "side" and the like, are used in conjunction with the drawings for purposes of clarity and are not intended to limit the present invention in any way, shape or form. In addition, the term "inlet" as used herein is interchangeable with "eyelet," "opening," "or "inlet opening," and is not intended to limit the inlet, eyelet, opening or inlet opening to any specific shape or form.

Figure 1:
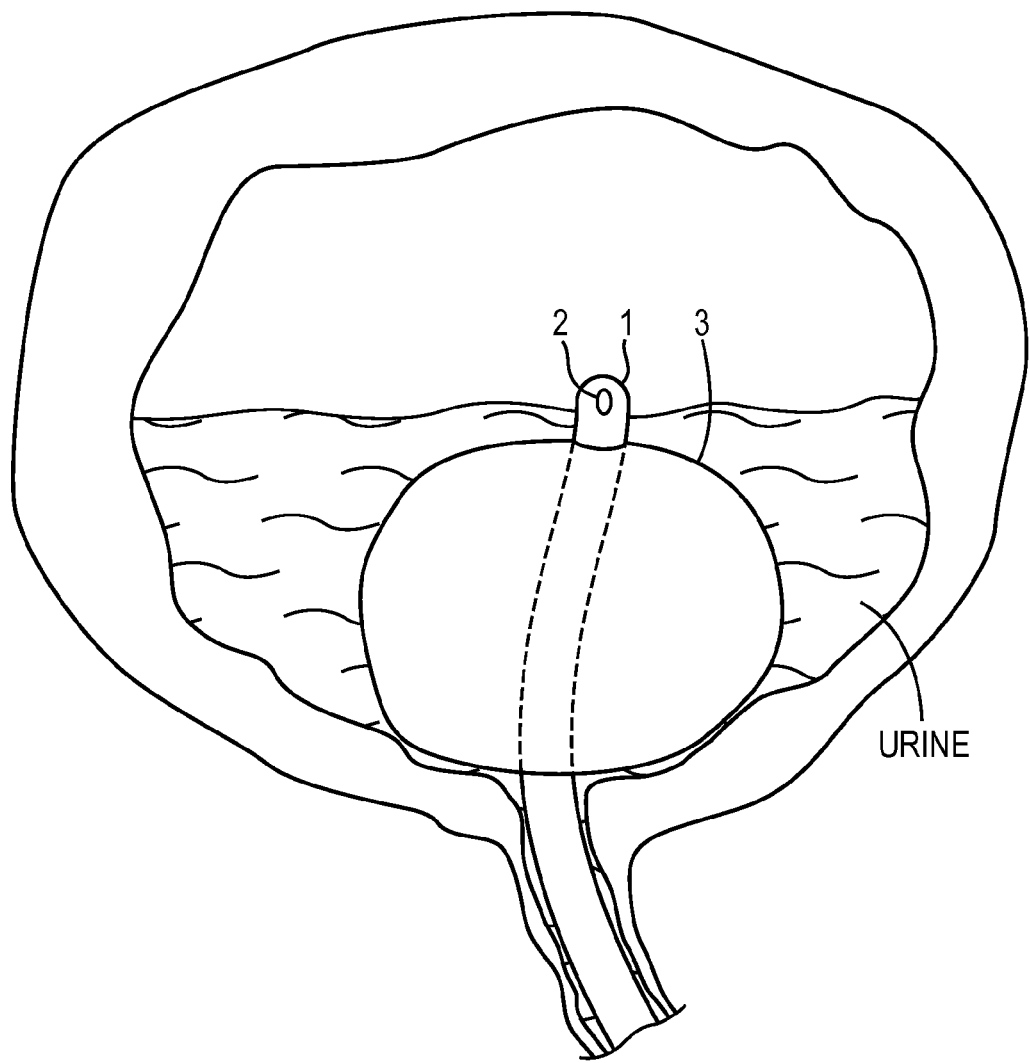
FIG. 1 is a depiction of a prior art Foley catheter in-situ.

Referring now to the drawings, FIG. 1 depicts a typical Foley catheter as it resides in its inflated position inside a urinary bladder. The single balloon 3 of the Foley catheter is retained inside the urinary bladder and continuously contacts the mucosal lining of the inner bladder wall. The Foley catheter tip 1 and urine inlet opening 2 extend past and above the single balloon. As the urine drains through the urine inlet opening 2, a residual volume of urine remains under the urine inlet opening and surrounding the single balloon 3 of the Foley catheter. This residual urine volume provides a point of proliferation for any microbes and fungi remaining in the urine. These microbes and fungi may then adhere to the tissue layers inside the bladder and invade the host tissue. Any proximal urine inlet lower on the catheter tip and closer to the single balloon 3 would be equally ineffective because the entire volume of urine would still be unable to escape through the urine inlet as long as it is positioned above the single balloon. As such, any positioning of the proximal urine inlet above the single balloon would not eliminate the pooling of urine around the perimeter of the single balloon. Thus, the proliferation of microbes and fungi would occur notwithstanding the position of the proximal urine inlet above the single balloon because a residual volume of urine would still remain.

The Foley catheter tip inside the urinary bladder also presents a significant mechanical risk to the catheterized patient. As FIG. 1 shows, the proximal tip 1 of the Foley catheter extends beyond the single balloon 3 and remains exposed to the inside of the urinary bladder. As the Foley catheter moves, or likewise as the patient moves, the proximal tip 1 of the Foley catheter may rub against, contact, irritate or otherwise damage the mucosal lining of the urinary bladder wall. Any damage to the mucosal lining of the wall renders this tissue susceptible to further damage by microbes or fungi and also provides a point of entry into the underlying tissue of the urinary bladder and patient's bloodstream. The damaged tissue of the urinary bladder is also exposed to the increased inoculum size of the microbes and fungi which have proliferated in the residual urine, thus increasing the likelihood of host infection. Also, as described above, the negative pressure differential between the drainage lumen of the Foley catheter and the inside of the urinary bladder may draw the mucosal lining of the urinary bladder into the urine inlet 2 of the Foley catheter thus further damaging the tissue lining the urinary bladder. The present invention cures these defects.

Figure 2:
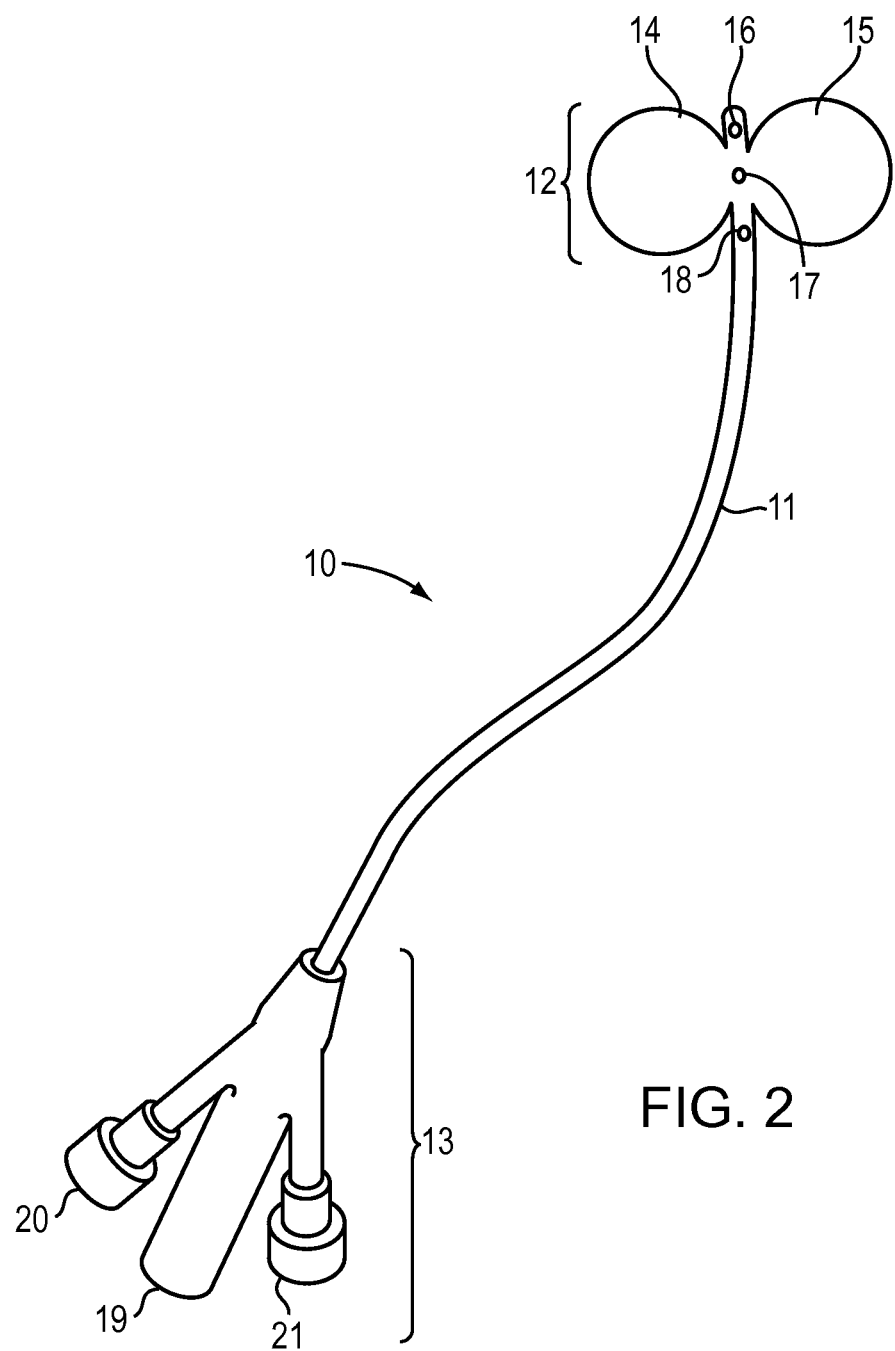
FIG. 2 is an elevation view of an illustrative embodiment of a catheter according to the present invention with the two balloons inflated.

An illustrative embodiment of a self-retaining urinary catheter according to the present invention is depicted in FIG. 2. The catheter 10 consists of a tube 11 with a closed proximal end 12 and an open distal end 13. The closed proximal end 12 may have a pointed or rounded tip as illustrated in FIG. 2. Other shapes of the proximal tip will be readily apparent to those of ordinary skill in the art. The length of the tube may vary and standard lengths are usually grouped in the categories of male, female and pediatric. The diameter may also vary, but must be sufficiently thick to allow for the embodiments of the invention without compromising the flexibility and strength of the tube. The closed proximal end 12 further consists of three urine inlet openings 16, 17, 18 and two balloons 14 and 15 arranged on opposite sides of the hollow tube 11. The shape of the inlet opening may vary and may be a teardrop, oval, racetrack, or the like, or any combination of shapes. In this particular embodiment, the urine inlet is an oval. Balloons 14 and 15 in FIG. 2 are illustratively two 5 mL balloons. However, depending on the application and the substance filling the balloon, e.g. air versus fluid, the balloon size may vary between about 0.1-10 mL. For example, in one embodiment used within the human urinary bladder, balloon sizes are about 5 mL each for a person of normal height and weight. As one skilled in the art may appreciate, the size of the balloons may vary by the size of a patient's bladder. One skilled in the art may also appreciate that the size of the balloons may vary in non-human embodiments. For example, if the size of the non-human bladder (and opening of the urethra into the bladder) is twice the size of a normal human, the size of the balloons may consequently be twice the size of the balloons described herein, for example, 20 mL or less. In other embodiments, the closed proximal end tip may also extend a small distance past the proximal portions of the tube, for example, about 0.5 cm, without compromising the shielding effect of the balloons.

As illustrated in FIGS. 3a and 3b, the balloons 14 and 15 expand perpendicular to the longitudinal axis Y of catheter tube 11 along the axis X at, for example, about similar distances from the closed proximal end of tube 11 such that the balloons 14 and 15 sufficiently protect and shield tube 11 from contacting the inner tissue, such as the mucosa, of the bladder, or in other embodiments, the inner tissue or mucosa of a body cavity, and shields the inlet or inlets from drawing any tissue or mucosa into inlets 16, 17 and 18. The balloons 14 and 15 expand along axis X as illustrated in FIGS. 3a and 3b and are located illustratively equal distances, or essentially equally distances, from the proximal tip of the catheter tube 11.

In FIG. 2, the proximal end 12 consists of three urine inlet openings at different levels in which urine inlet opening 16 is located at about the level of the proximal sides of the two balloons 14 and 15, a second urine inlet opening 17 is located at about midway between the two balloons 14 and 15 and a third urine inlet opening 18 is located at about the level of the distal sides of the two balloons 14 and 15. The particular number of inlet openings may vary. For example, in another embodiment of the present invention, the catheter may contain a single inlet at about the level of the distal sides of the two balloons or closer to about the midway point between the two balloons. In yet another embodiment of the present invention, the catheter may contain more than three inlets arranged in any number of configurations on the proximal end 12 of the catheter 10.

Other embodiments and arrangements of an inlet or inlets are positioned appropriately to prevent the mucosal lining, or any other tissue, from being drawn into the inlet or inlets. For example, as illustrated in FIG. 2, the urine inlets 16, 17 and 18 and balloons 14 and 15 are positioned appropriately on the catheter 10 to prevent the catheter tip from rubbing against the mucosal layer of the inner bladder wall and to prevent the mucosal layer from being drawn into either the proximal or distal urine inlets. In other embodiments, the placement of the inlets may vary and the proximal inlet, for example, may be closer to the proximal tip of the catheter whereas the distal inlet may be located further towards the distal end of the catheter within the body cavity. The inlets may also open into the main lumen only on one side of the tube or the inlets may pass completely through the tube thus creating openings on opposite sides of the tube. The inlets may also be arranged in alternating positions on the tube such that, for example, in a catheter with three inlets, the proximal inlet and the distal inlet open on the same side of the tube and the middle inlet located between the two balloons opens on a different side of the tube. Some inlets may also open only on one side of the tube while others may pass completely through the tube.

In FIG. 2, the distal end 13 of the catheter 10 consists of a urine outlet port 19. The urine outlet port 19 may be a Push/Pull or Screw type connection for easier handling of the connection. Other connection systems will be recognized by those skilled in the art. In other embodiments, the outlet port may be an outlet port for other bodily fluids or gases. The distal end 13 also consists of two infusion ports 20 and 21 for infusion of a substance, such as sterile liquid or air, for inflation of balloons 14 and 15. The infusion ports 20 and 21 may be contraction or one-way valves. Other similar systems for the infusion ports will be recognized by those skilled in the art. Infusion is accomplished by needles, syringes or like devices which may be connected to the infusion ports 20 and 21 to fill the balloons 14 and 15. In other embodiments, there may be more than two infusion ports on the distal end that are appropriately interconnected to the two secondary lumens. In yet other embodiments, there may be more than one outlet port appropriately interconnected to the main lumen.

FIG. 4 is a cross-sectional view of the catheter tube 11 showing a main lumen 23 for the exiting of the urine through the catheter 10. This main lumen 23 may also be referred to as a urine channel or urine drainage canal. The main lumen 23 is interconnected with the urine outlet port 19 such that, in this illustrative embodiment, urine flows from the bladder through the main lumen 23 and out the urine outlet port 19. The two secondary lumens 24 and 25 in FIG. 4 are interconnected with the two infusion ports 20 and 21 such that balloons 14 and 15 are inflated by sterile liquid or air carried down the tube 11 of catheter 10 through secondary lumens 24 and 25. The two secondary lumens 24 and 25 may also be referred to as infusion channels or inflation passage channels and may extend longitudinally down the catheter tube on opposite sides of the main lumen (e.g. 180° from each other and perpendicular to the longitudinal axis) or may extend closer to each other longitudinally down the catheter tube (e.g. less than 180° from each other and perpendicular to the longitudinal axis).

Figure 5:
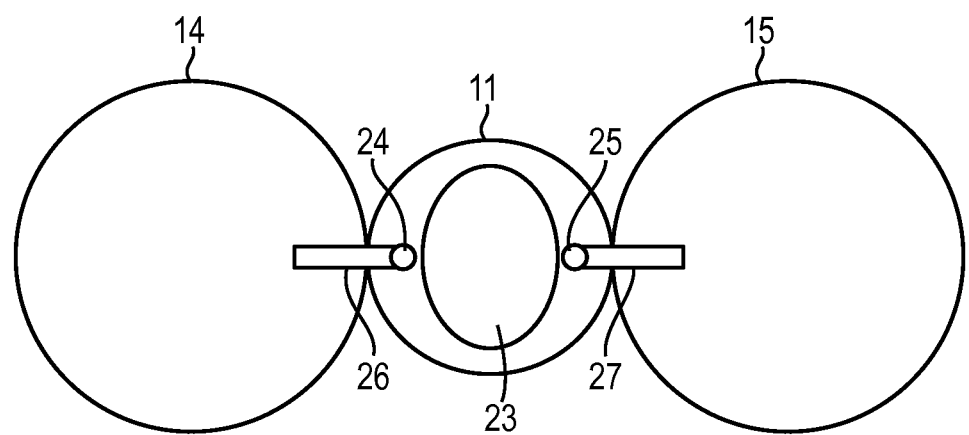
FIG. 5 is a cross-sectional view of the proximal catheter tip of FIG. 2 with the balloons in the inflated position.

FIG. 5 is a cross-sectional view of the proximal end of the catheter 10. Balloons 14 and 15 are supplied and filled with sterile liquid or air from secondary lumens 24 and 25 by means of connection ports 26 and 27. Connection ports 26 and 27 may be simple openings, apertures or valve-type openings. Other connection systems will be recognized by those skilled in the art. The balloons may also be connected directly to the secondary lumens. The balloons are generally attached to the secondary lumens, meaning that the balloons may be directly connected or contiguous with the secondary lumens or may be connected via various types of connected ports.

Figure 6A:
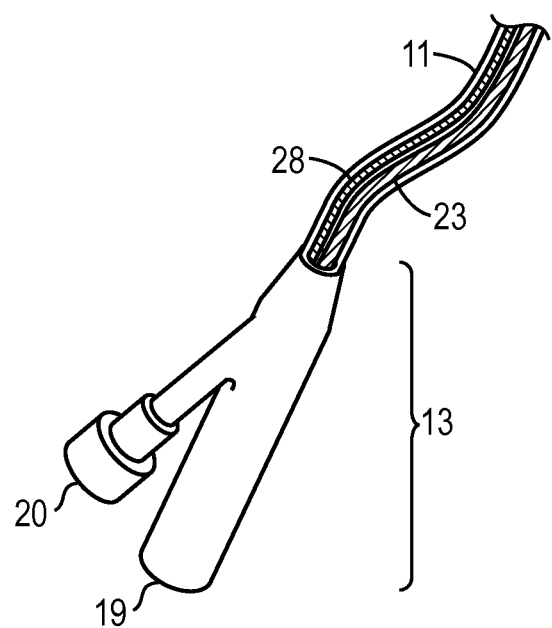
FIGS. 6A and 6B are views of an illustrative embodiment with one infusion port and one secondary lumen.
Figure 6B:
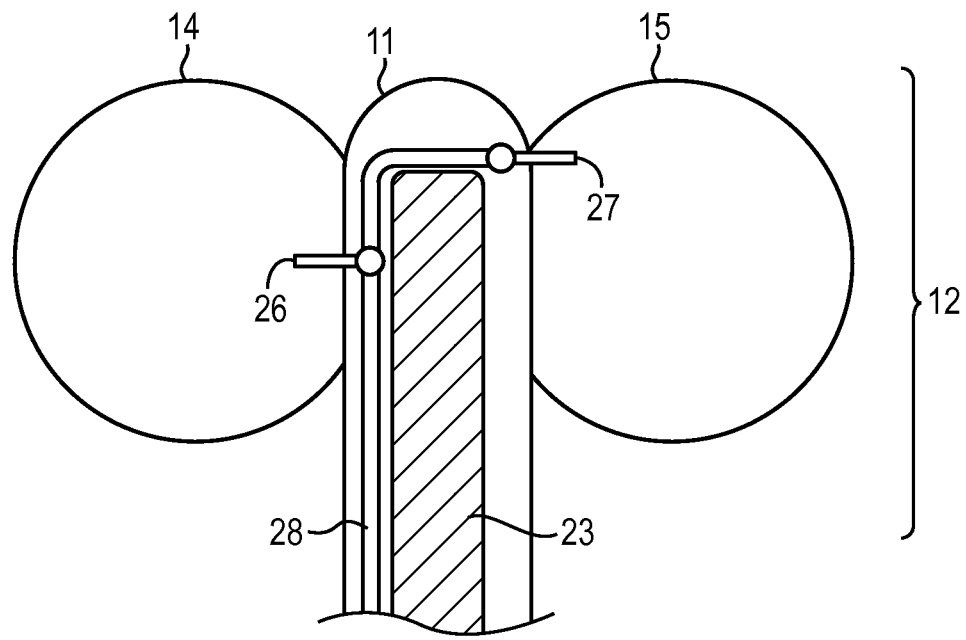

As illustrated in FIG. 6A, another embodiment of the invention may have one infusion port 20 connected to one secondary lumen extending longitudinally from the distal end 13 to the proximal end (not shown) of the catheter tube 11. FIG. 6B illustrates the proximal end 12 of this embodiment without the inlets depicted. The secondary lumen 28 connects to, or attaches to, connection port 26 and continues past and loops around the proximal portion of main lumen 23 to connect to, or attach to, connection port 27 located illustratively slightly above the main lumen 23 on the proximal end of catheter tube 11. In other embodiments, connection port 27 may be located opposite the catheter tube 11 and level with connection port 26. Balloons 14 and 15 are inflated by the sterile liquid or air proceeding through the secondary lumen 28 through connection ports 26 and 27. As will be apparent to those skilled in the art, the secondary lumen 28 may be in different positions around the main lumen 23, for example, closer to one side of a particular balloon, without departing from the scope of the invention. One of ordinary skill in the art will also recognize sterile liquid or air may be infused into balloons 14 and 15 by various different connection methods such as different arrangements of valves, openings, or similar connection lumens or channels. In other embodiments, instead of looping around the main lumen, the secondary lumen may branch off into two additional secondary lumens to appropriately connect with, or attach to, respective connection ports to thus fill or inflate the balloons.

The catheter tube 11 of the present invention may be constructed from various materials, including, but not limited to, latex, vinyl, silicone, PVC or any other non-toxic semi-rigid material. The balloons of the invention may be constructed from various materials including, but not limited to, materials of low compliance such as polyurethanes, polyethylenes, polyvinylchlorides, polyamides or polyethylene teraphthalates, or copolymer admixtures, such as a low density polyethylenes and ethylene-vinylacetate chlorides. The balloons may also be constructed from mixtures of the aforementioned materials. The balloon material is illustratively biologically inert and may have a thickness of about 1-70 µm, and, in some embodiments, have an illustrative thickness of 3-35 µm. The balloons may also be coated with antimicrobial substances such as antibiotics, antiseptics, bactericides or other similar technologies, to prevent the formation of biofilms on the surface of the balloons and to prevent the subsequent proliferation of microbes and fungi. The balloons may also be of identical size or may vary in size according to the particular application. In an illustrative embodiment, the balloons are of equal size. The balloons may also be reversibly expandable balloons.

The balloons are located at about just distal to the proximal tip of the catheter to about 2 cm from the proximal tip of the catheter for circularly or about circularly-expanding 0.1-10 mL balloons. The radius of one circularly expanding 5 mL balloon is about 1 cm. Locations of the balloons from the proximal tip are measured from the midpoint of the balloons to the proximal tip of the catheter tube. In other embodiments the balloons may expand in oblong shapes and may be located about at about just distal to the proximal tip of the catheter to about 3 cm depending on the shape of the 0.1-10 mL balloons. The balloons may also be located at certain, equal fixed distances from the proximal end of the catheter or may be located at varying distances, thus skewing or tailoring the alignment of the catheter to suite a particular position within the bladder. For example, the two balloons may both be located from about just distal to the proximal tip of the catheter to about 1 cm from the proximal tip, as measured from the proximal tip to the midpoint of the balloon; or one balloon may illustratively be located 1 cm from the proximal tip while the other is located 1.2 cm from the proximal tip. The two balloons are oriented appropriately on their respective sides of the catheter tube, as they appear longitudinally along the catheter tube axis, to sufficiently protect the catheter tube from contacting the mucosal lining of the body cavity and to prevent any in-drawing of the mucosal lining into any inlet or inlets. In addition, the balloons may be oriented opposite each other on the catheter tube (e.g. 180° from each other and perpendicular to the longitudinal axis of the catheter tube) or may be oriented closer to each other on the same side of the catheter tube, for example, at positions less than 180° from each other. In another illustrative embodiment, both balloons are located equidistant from the proximal tip at about 1-2 cm, for example, 1 cm, from the proximal tip of the catheter tube, and are illustratively on opposite sides of the catheter tube approximately 180° from each other.

In other embodiments of the invention, the balloons may vary in attachment and placement on the catheter. In one embodiment, a membrane sleeve made of easily expandable material, including, for example, any of the materials listed above, is placed over holes or apertures on the surface of the catheter near the proximal end of the catheter, which open into and correspond to the secondary lumens and expand upon infusion of sterile liquid or air. In another embodiment of the invention, the balloons may be housed in two separate rectangular expandable membranes affixed to opposite sides of the proximal end of the catheter over holes or apertures on the surface of the catheter, which open into and correspond to the secondary lumens. The membrane sleeve and rectangular expandable membranes may be secured in place and affixed to the catheter body by thermal bonding, dipping, ultrasonic bonding or any other currently available method of bonding. The membrane sleeve and rectangular expandable membranes may be located about 1 cm from the proximal tip of the catheter. As the sterile liquid or air is infused into the secondary lumens, the expandable portions of the membrane sleeve, or rectangular expandable membranes, covering the holes or apertures, inflate appropriately to retain the proximal end of the catheter within the bladder.

Figure 7:
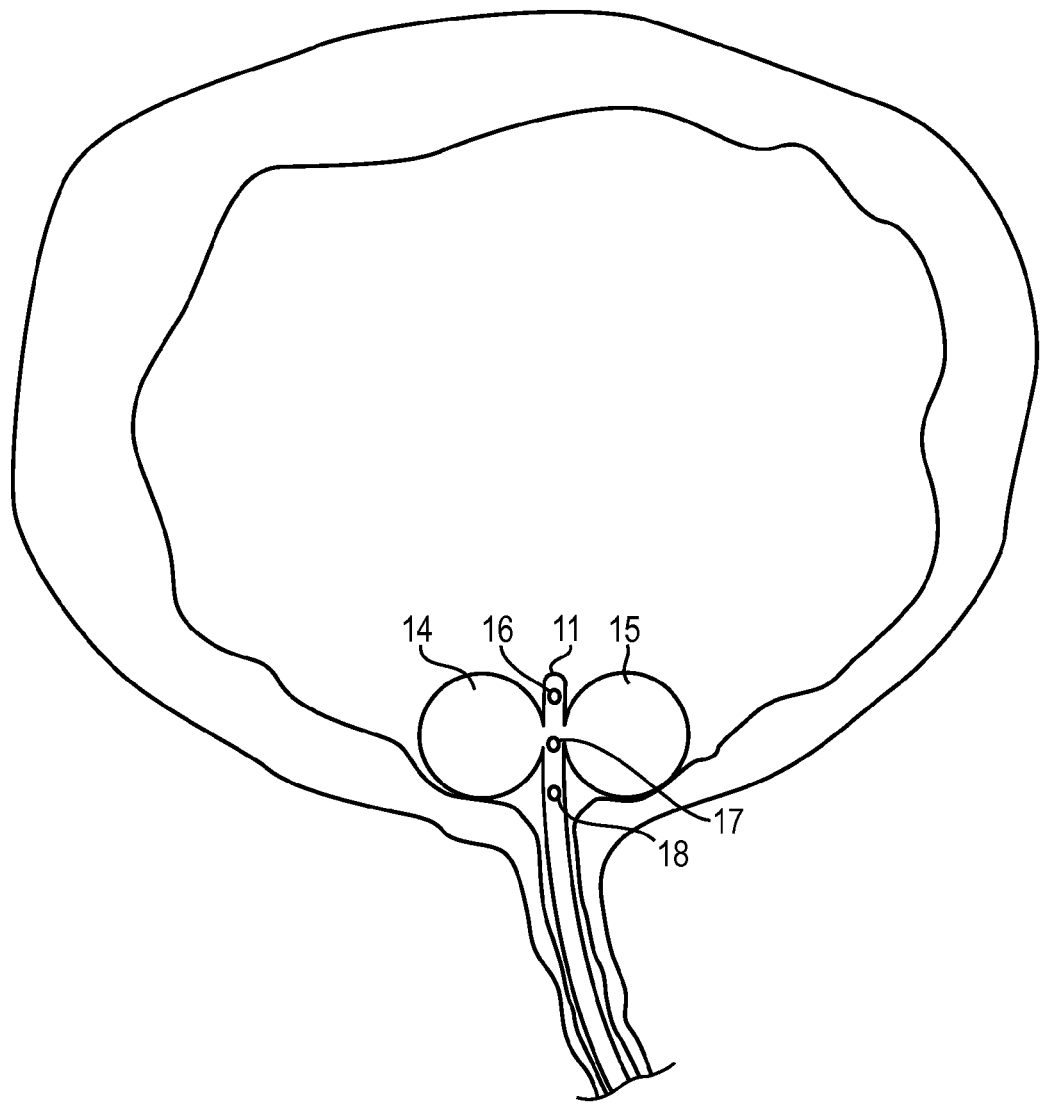
FIG. 7 is a view of the catheter of FIG. 2 in an inflated position inside a urinary bladder.

FIG. 7 illustrates one embodiment of the present invention as it is used in-situ within the urinary bladder as an indwelling urinary catheter. The two proximally located balloons 14 and 15 act as retention members to retain the catheter within the bladder. Other embodiments may employ at least one retention member that is not a balloon, but is functionally similar to a balloon, such as an extending arm or member. In this embodiment, the balloons 14 and 15 are 5 mL balloons located 1 cm, measured from the midpoint of the balloons to the proximal tip, and opposite each other on the proximal end of the urinary catheter (180° from each other and perpendicular to the longitudinal axis of the catheter tube). The proximal end also contains three oval-shaped urine inlet openings 16, 17 and 18. The proximal urine inlet opening 16 is located appropriately near the proximal tip of the urinary catheter, but about level with the proximal sides of the two balloons 14 and 15 thus shielding urine inlet opening 16 from contact with the mucosal lining of the inner urinary bladder wall. The second urine inlet opening 17 is located about midway between the two balloons 14 and 15. The third inlet opening 18 is located below the second urine inlet opening 17, but about level with the distal sides of the two balloons 14 and 15 thus shielding the third urine inlet opening 18 from contact with the mucosal lining of the inner urinary bladder wall. The balloons 14 and 15 are of sufficient size and placement on the catheter tube 11 to allow for appropriate retention of the catheter within a body cavity, such as a urinary bladder, and also to prevent the contact of the proximal catheter tip with the mucosal lining of the body cavity and the suction of the mucosal lining into any inlet. Other embodiments may contain different numbers of inlets, including, for example, only a single inlet at, level with, or near the distal portion of the two balloons, such that the two balloons do not allow the mucosal lining to be drawn into the inlet; or two inlets with one located as described and an additional inlet at, level with, or near the proximal portion of the two balloons, such that the two balloons do not allow any mucosal tissue to be drawn into this inlet. Other embodiments may contain two inlets with one inlet located at, level with, or near the distal portion of the two balloons and a second inlet located at, level with, or near the proximal portion of the two balloons such that both inlets are shielded from the mucosal lining of the body cavity by the two balloons, but are effective in draining the body cavity of any fluids.

Figure 8A:
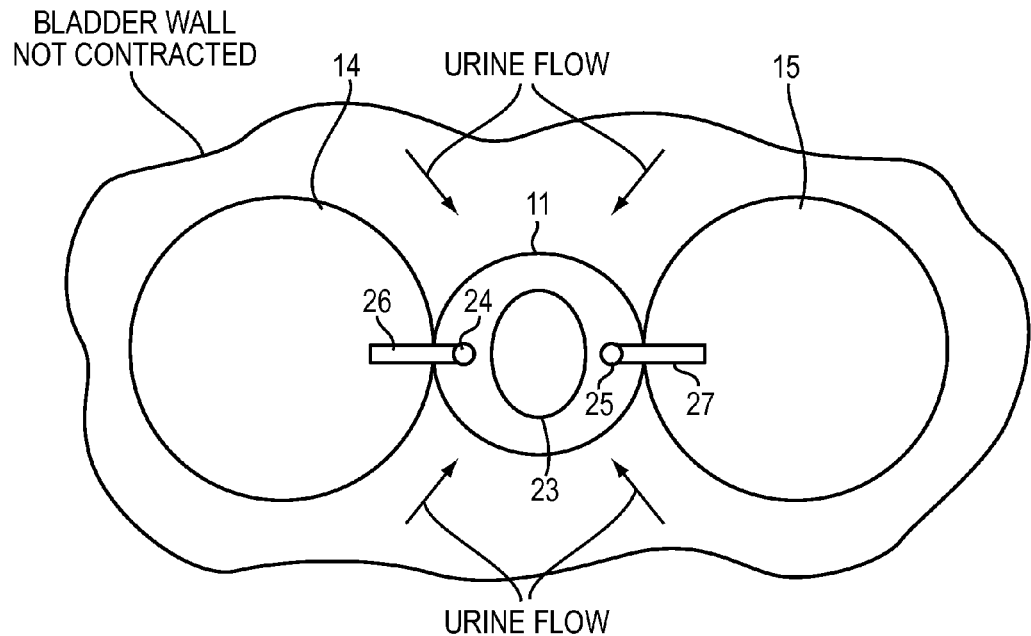
FIG. 8A is a cross-sectional view of FIG. 7 in which the bladder is not contracted.
Figure 8B:
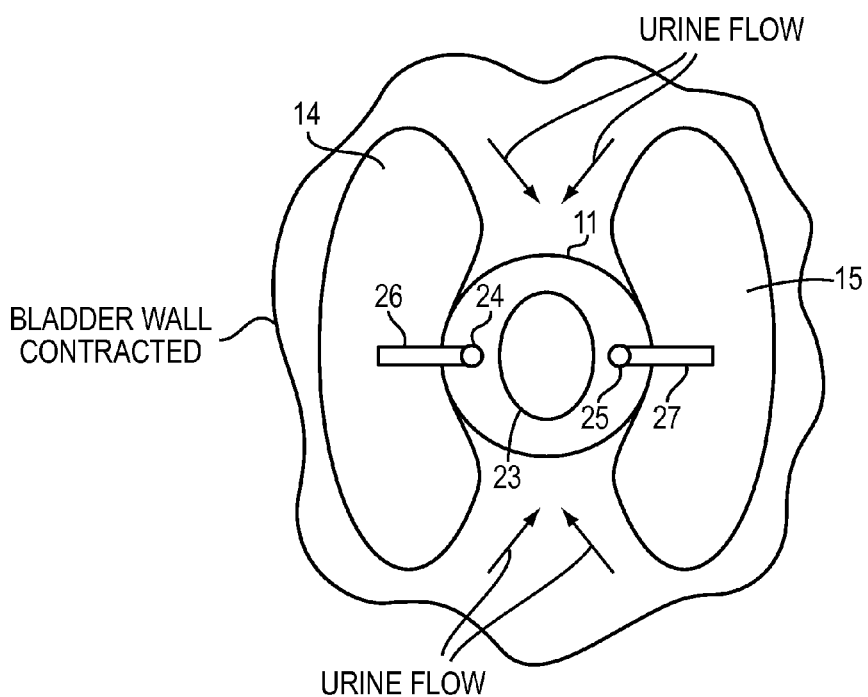
FIG. 8B is a cross-sectional view of FIG. 7 in which the bladder is contracted.

The two balloons of the present invention also function to provide channels for bodily fluids to flow into the inlet openings between the two balloons. As illustrated in FIG. 8A, fluid, such as urine, is able to pass between the two balloons 14 and 15 on each side of the catheter tube 11 into the inlets thus allowing for complete draining of fluid. Also, as illustrated in FIG. 8B, when, for example, the bladder contracts, the mucosal lining of the inner urinary bladder wall surrounds the two balloons 14 and 15, but urine is able to pass through the channels formed between the spacing of the two balloons 14 and 15 and thus is able to exit the bladder through, for example, the distally located urine inlet opening 18 illustrated in FIG. 7. The present invention thus overcomes the drawbacks of prior art devices by facilitating the complete voiding of body cavities, eliminating the damage caused by the proximal tip contacting the tissue lining of body cavities and eliminating the damage caused by the in-drawing of the mucosal lining into the urine inlet openings. Damage and infection to body cavities is thus drastically reduced with the present invention and the need for subsequent medical intervention is also drastically reduced. Moreover, the limited surface area of the two balloons significantly reduces the ability of microorganisms to develop biofilms, which thus slows the rate of proliferation of these microorganisms and reduces the risk of infection in body cavities.

The present invention is described in terms of illustrative embodiments. However, it will be understood that the present invention is not limited to illustrative embodiments as described herein. For example, the present invention may be used to facilitate the removal of fluid from the bladder, kidney, abdominal abscesses, thoracic cavity, intestinal tract, or any physiological or pathological body cavity. The invention may also facilitate the removal of any gases that have also accumulated in any body cavities. In addition, the catheter may be retained within body cavities for short periods of time, such as a few minutes or a few hours, or extended periods of time, such as a day, multiple days, weeks, months or years. It will also be understood that the present invention may be equally effective in veterinary medicine to drain fluid from body cavities within animals. Changes to the illustrative embodiments described above may be made without departing from the scope and intent of this invention as described herein and in the claims. The drawings are not drawn to scale and are not intended to limit the full scope of the invention.

What is claimed is:

1. An apparatus for insertion into a body cavity comprising: a catheter of predetermined length and width having an open distal end and a closed proximal end; a main lumen and two secondary lumens extending longitudinally from the open distal end to the closed proximal end; the open distal end having at least one outlet port interconnected with the main lumen and at least two infusion ports interconnected with the two secondary lumens; the proximal end having at least one inlet, and two spherical balloons, the two spherical balloons configured to inflate so as to form channels between the two spherical balloons for the removal of fluid through the at least one inlet, the channels being open to an interior of the body cavity along entire lengths of the channels.

2. The apparatus of claim 1 wherein the catheter is an indwelling urinary catheter.

3. The catheter of claim 1 wherein at least one of the two spherical balloons is about 5 mL.

4. The catheter of claim 1 wherein the two spherical balloons are located at about equal distances from the closed proximal end.

5. The apparatus of claim 1 wherein an inlet is located between the two spherical balloons.

6. A catheter system comprising: a flexible tube of predetermined length and width having an open distal end with at least one infusion port and at least one outlet port and a closed proximal end with at least one inlet; and two spherical retention members on the closed proximal end, the two spherical retention members configured to inflate so as to form channels between the two spherical retention members for the removal of fluid through the at least one inlet, the channels being open to an interior of the body cavity along entire lengths of the channels.

7. The catheter system of claim 6 wherein the catheter is an indwelling urinary catheter.

8. The catheter system of claim 6 wherein the two spherical retention members are about 0.1-10 mL balloons.

9. The catheter system of claim 6 wherein the two spherical retention members are comprised of membrane sleeves or rectangular, circularly-expandable membranes.

10. The catheter system of claim 6 wherein at least one of the two spherical retention members is a reversibly expandable balloon.

11. The catheter system of claim 6 wherein at least one of the two spherical retention members has a membrane thickness of 3-35 µm.

12. The catheter system of claim 6 wherein the at least one infusion port is one infusion port.

13. A method of draining a body cavity comprising: inserting into a body cavity a catheter comprising a flexible tube of predetermined length and width having an open distal end with at least one infusion port and at least one outlet port, and a closed proximal end with at least one inlet and two spherical balloons; inflating the two spherical balloons so as to form channels between the two spherical balloons for the removal of fluid through the at least one inlet, the channels being open to an interior of the body cavity along entire lengths of the channels; and draining the body cavity through the at least one inlet at the proximal end of the catheter.

14. The method of claim 13 wherein the fluid is drained through an inlet located about level with a distal portion of the two spherical balloons.

15. The method of claim 13 wherein the two spherical balloons are located about equal distances from the closed proximal end.

16. The method of claim 13 wherein the body cavity is at least one of a urinary bladder, kidney, abdominal abscess, thoracic cavity and intestinal tract.

17. The method of claim 13 wherein the body cavity is a pathological body cavity.

18. The method of claim 13 wherein the body cavity is an animal body cavity.

19. The method of claim 13 wherein the body cavity is a human body cavity.

20. The method of claim 13 wherein an inlet is located midway between the two spherical balloons.

21. An apparatus for insertion into a body cavity comprising: a catheter of predetermined length and width having an open distal end and a closed proximal end; the proximal end having at least one inlet, and two spherical balloons, the two spherical balloons configured to expand perpendicularly to a longitudinal axis of the catheter; a main lumen and one secondary lumen extending longitudinally from the open distal end to the closed proximal end, the secondary lumen interconnected with the two spherical balloons; the open distal end having at least one outlet port interconnected with the main lumen and at least one infusion port interconnected with the secondary lumen.

\* \* \* \* \*